(12) United States Patent
Gomes (10) Patent No.: US 11,020,183 B2
(45) Date of Patent: Jun. 1, 2021

(54) METHOD FOR DESIGNING A PATIENT SPECIFIC ORTHOPAEDIC DEVICE

(71) Applicant: EOS IMAGING, Paris (FR)

(72) Inventor: Christophe Gomes, Paris (FR)

(73) Assignee: EOS IMAGING, Paris (FR)

( * ) Notice: Subject to any disclaimer, the term of this patent is extended or adjusted under 35 U.S.C. 154(b) by 207 days.

(21) Appl. No.: 14/893,749

(22) PCT Filed: May 30, 2013

(86) PCT No.: PCT/IB2013/001773
§ 371 (c)(1),
(2) Date: Nov. 24, 2015

(87) PCT Pub. No.: WO2014/191790
PCT Pub. Date: Dec. 4, 2014

(65) Prior Publication Data
US 2016/0100907 A1    Apr. 14, 2016

(51) Int. Cl.
*A61B 34/10*    (2016.01)
*G06F 17/50*    (2006.01)
*A61B 90/00*    (2016.01)

(52) U.S. Cl.
CPC ........ *A61B 34/10* (2016.02); *A61B 2034/102* (2016.02); *A61B 2034/108* (2016.02); *A61B 2090/376* (2016.02)

(58) Field of Classification Search
CPC .............. A61B 34/10; A61B 2034/102; A61B 2034/108; A61B 2090/376
See application file for complete search history.

(56) References Cited

U.S. PATENT DOCUMENTS

| 8,715,291 B2 | 5/2014 | Park et al. |
| 8,968,320 B2* | 3/2015 | Park ....................... A61B 5/055 606/88 |
| 2008/0262812 A1* | 10/2008 | Arata .................... A61F 2/3859 703/11 |

(Continued)

FOREIGN PATENT DOCUMENTS

| EP | 1168249 B1 | 1/2002 |
| EP | 2436321 | 4/2012 |

(Continued)

OTHER PUBLICATIONS

International Search Report and Written Opinion dated Jan. 31, 2014 for Application No. PCT/IB2013/001773.

(Continued)

Primary Examiner — Christine A Enad
(74) Attorney, Agent, or Firm — Frost Brown Todd LLC (57) ABSTRACT

A method for designing a patient specific orthopaedic device intended for an osteoarticular structure of a patient, based on at least two two-dimensional radiographic images of the osteoarticular structure taken respectively in two offset image-taking directions, comprising the following steps: b) locating anatomical points on the radiographic images; c) determining at least one three-dimensional geometrical feature of the patient by matching the anatomical points b) located at step b); d) determining at least one three-dimensional size parameter of the orthopaedic device based on the geometrical feature of the patient determined at step c).

17 Claims, 5 Drawing Sheets

(56) References Cited

U.S. PATENT DOCUMENTS

| | | | | |
|---|---|---|---|---|
| 2009/0138020 | A1* | 5/2009 | Park | A61B 5/055 606/88 |
| 2009/0157083 | A1* | 6/2009 | Park | A61B 5/055 606/88 |
| 2010/0076563 | A1* | 3/2010 | Otto | A61B 5/103 623/20.14 |
| 2010/0177948 | A1* | 7/2010 | Le Bras | A61B 5/1075 382/132 |
| 2010/0217109 | A1* | 8/2010 | Belcher | A61B 5/055 600/410 |
| 2010/0292963 | A1* | 11/2010 | Schroeder | A61F 2/30 703/1 |
| 2011/0093108 | A1* | 4/2011 | Ashby | A61B 19/50 700/103 |
| 2012/0289965 | A1* | 11/2012 | Gelaude | A61B 17/15 606/87 |
| 2012/0310400 | A1* | 12/2012 | Park | A61B 5/055 700/98 |

FOREIGN PATENT DOCUMENTS

| | | |
|---|---|---|
| FR | 2749402 A | 12/1997 |
| FR | 2754068 A | 4/1998 |
| WO | WO 2009/004410 | 1/2009 |
| WO | WO 2011/080260 | 7/2011 |
| WO | WO 2013/062849 | 5/2013 |

OTHER PUBLICATIONS

Prost, Soléne, et al. "'Patient-specific' rods in the management of adult spinal deformity. One-year radiographic results of a prospective study about 86 patients." *Neurochirurgie* 66.3 (2020): 162-167.

Sadrameli, Saeed S., et al. "Utility of Patient-Specific Rod Instrumentation in Deformity Correction: Single Institution Experience." *Spine Surgery and Related Research* (2020): 2019-0101.

* cited by examiner

METHOD FOR DESIGNING A PATIENT SPECIFIC ORTHOPAEDIC DEVICE

FIELD OF THE INVENTION

The instant invention relates to a method for designing a patient specific orthopaedic device from information obtained from a limited number of projected radiographs.

BACKGROUND OF THE INVENTION

Orthopaedic surgery relies upon anatomical pre-operative data obtained from imaging exams. In most cases, such exams are planar X-ray radiographs that allow to measure patient anatomical parameters and plan an adequate surgery.

Such approaches can lead to the selection and positioning of a given implant, or to the planning of a given correction to spinal disorders from pre-operative data.

Most recently, numerous techniques have been developed to derive patient specific devices from 3D information obtained from CT or MRI exams. These can be, in particular, patient specific surgical tools such as cutting guides or patient customized implants.

However, these techniques are limited by their cost and by their inability to reflect the patient natural weight-bearing position, leading to potential misalignment which is critical to post-operative outcome.

SUMMARY OF THE INVENTION

It is an object of the present invention to provide a method for designing a patient specific orthopaedic device which is accurate, reliable and inexpensive.

To this aim, it is provided a method for designing a patient specific orthopaedic device intended for an osteoarticular structure of a patient, based on at least two two-dimensional radiographic images of the osteoarticular structure taken respectively in two offset image-taking directions, comprising the following steps:
  b) locating anatomical points on the radiographic images;
  c) determining at least one three-dimensional geometrical feature of the patient by matching the anatomical points located at step b);
  d) determining at least one three-dimensional size parameter of the orthopaedic device based on the geometrical feature of the patient determined at step c).

With these features, the method of the present invention enables to obtain, reliably and inexpensively, an accurate orthopaedic device which is specific to the patient.

In some embodiments of the method of the invention, one might also use one or more of the following features:
  the method further comprises, before step b), a step of a) taking the radiographic images simultaneously;
  the method further comprises, before step b), a step of a) taking the radiographic images successively;
  step c) comprises reconstructing a three-dimensional shape of at least a portion of the osteoarticular structure based on the anatomical points located at step b);
  the three-dimensional size parameter of the orthopaedic device is determined in a three-dimensional space specific to the patient and chosen among a three-dimensional length, a three-dimensional angle, a three-dimensional curvature, a three-dimensional surface and a three-dimensional volume;
  the three-dimensional size parameter of the orthopaedic device is determined in a plane of a three-dimensional space specific to the patient, said plane being different from each of the planes of the radiographic images;
  the orthopaedic device is chosen among an implant and a surgical instrument for the placement of an implant or of another surgical instrument;
  the orthopaedic device is a spinal implant, a geometrical feature of the pelvis of the patient is determined at step c) and a length and/or a curvature of the spinal implant is determined at step d);
  the orthopaedic device is a hip implant and a geometrical feature of the pelvis and/or femur of the patient is determined at step c);
  the orthopaedic device is a knee implant and a geometrical feature of the femur and/or tibia of the patient is determined at step c);
  the orthopaedic device is a shoulder implant and a geometrical feature of the humeral head and/or scapula of the patient is determined at step c);
  the orthopaedic device is a surgical instrument intended to guide a bone cutting tool, and a geometrical feature of the pelvis, femur and/or tibia of the patient is determined at step c);
  the method further comprises a step of e1) forming the orthopaedic device according to the size parameter determined at step d); and
  the method further comprises a step of e2) selecting the orthopaedic device among a plurality of orthopaedic devices based on the size parameter determined at step d).

It is a further object of the present invention to provide a computer program product for a data-processing system comprising a set of instructions which, when loaded into the data-processing system, causes the system to perform the steps of the method as described above.

It is another object of the present invention to provide an apparatus for designing a patient specific orthopaedic device intended for an osteoarticular structure of a patient, based on at least two two-dimensional radiographic images of the osteoarticular structure taken respectively in two offset image-taking directions, comprising:
  means for locating anatomical points on the radiographic images;
  means for determining at least one three-dimensional geometrical feature of the patient by matching the anatomical points located by the locating means;
  means for determining at least one three-dimensional size parameter of the orthopaedic device based on the geometrical feature of the patient determined by the determining means.

In an embodiment of the apparatus of the invention, the apparatus further comprises means for taking the radiographic images.

BRIEF DESCRIPTION OF THE DRAWINGS

Other characteristics and advantages of the invention will readily appear from the following description of several of its embodiments, provided as non-limitative examples, and of the accompanying drawings.

On the drawings.

On the different Figures, the same reference signs designate like or similar elements.

DETAILED DESCRIPTION

Figure 1:
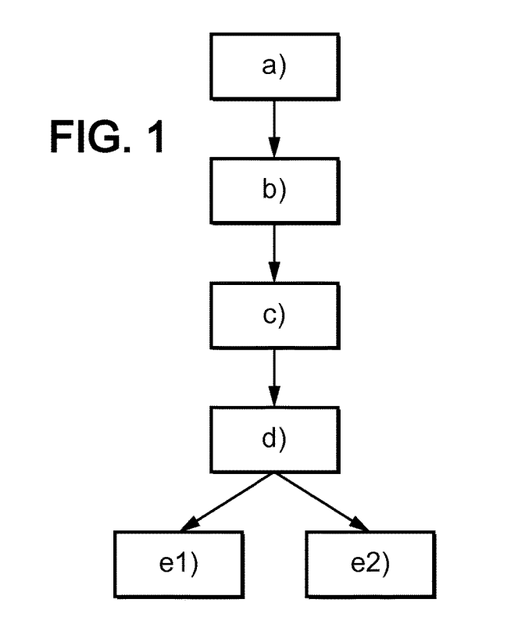
FIG. 1 is a flow chart showing the steps of a method for designing a patient specific orthopaedic device according to the invention.

FIG. 1 shows the different steps of a method for designing a patient specific orthopaedic device for an osteoarticular structure of a patient according to the invention, based on at least two two-dimensional radiographic images of the osteoarticular structure taken respectively in two offset image-taking directions.

The method comprises at least the following steps:

b) locating anatomical points on the radiographic images;

c) determining at least one three-dimensional geometrical feature of the patient by matching the anatomical points located at step b);

d) determining at least one three-dimensional size parameter of the orthopaedic device based on the geometrical feature of the patient determined at step c).

Optionally, the method can comprise, before step b), a step of a) taking the radiographic images simultaneously or successively.

The radiographic images used in the method are geometrically calibrated.

Optionally, the method can comprise a step of e1) forming the orthopaedic device according to the size parameter determined at step d), or a step of e2) selecting the orthopaedic device among a plurality of orthopaedic devices based on the size parameter determined at step d).

By "three-dimensional" geometrical feature and "three-dimensional" size parameter, it is meant respectively a feature and a parameter which are determined in a three-dimensional space or frame of reference which is specific to the patient and thus related to the osteoarticular structure under consideration.

The geometrical feature and the size parameter can also be determined in a plane of this three-dimensional space specific to the patient, for example in the sagittal plane of the patient, which is different from the planes of the radiographic images.

Each step a), b), c), d), e1) and e2) will be described below in greater details.

In the example described here, the method is carried out by a radiographic apparatus 1 for three-dimensional reconstruction.

Figure 2:
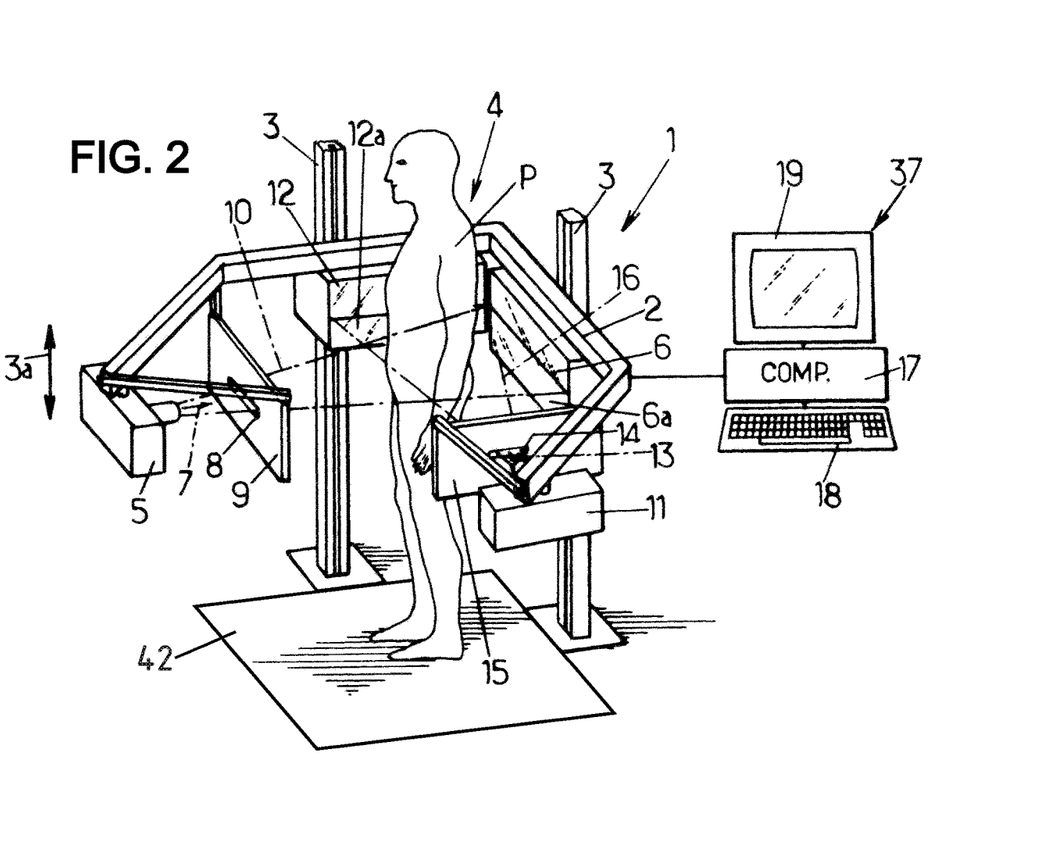
FIG. 2 is a schematic perspective view of an apparatus for designing a patient specific orthopaedic device according to the invention.

With reference to FIG. 2, the apparatus 1 comprises a moving frame 2 displaceable under motor drive along vertical guides 3 in both directions of translation 3a.

The frame surrounds a field of observation 4 in which a patient P may be placed, e.g. standing, for observing an osteoarticular structure of the patient when in the standing position, which may be important for analyzing the bone alignments in the weight-bearing position.

The moving frame 2 carries a first radiological source 5 and a first detector 6 which is placed facing the source 5 beyond the field 4, and which comprises at least one horizontal line 6a of detector cells. By way of example, the detector 6 may be a gas detector responsive to low doses of radiation, e.g. as described in documents FR-A-2 749 402 or FR-A-2 754 068. Naturally, other types of detectors may optionally be used in the context of the present invention.

The radiological source 5 is adapted to emit ionizing radiation, in particular X-rays, suitable for being detected by the detector 6 in an image-taking direction 7 that is antero-posterior or postero-anterior relative to the patient P, the rays passing through a horizontal slit 8 made through an aiming mask 9 such as a metal plate in order to generate a horizontal beam 10 of ionizing radiation in the field of observation 4.

The moving frame 2 also carries a second radiological source 11 similar to the source 5 and a second detector 12 similar to the detector 6, disposed facing the source 11 beyond the field 4, and comprising at least one horizontal line 12a of detector cells.

The radiological source 11 is adapted to emit ionizing radiation in an image-taking direction 13 that is lateral relative to the patient P, passing through a horizontal slit 14 formed in an aiming mask 15 such as a metal plate in order to generate a horizontal beam 16 of ionizing radiation in the field of observation 4.

Naturally, there could be more than two radiological sources and detectors. In addition, the image-taking directions 7 and 13 could, where appropriate, be other than mutually perpendicular. For example, it is possible to provide an angle of about 30° between these image-taking directions. Moreover, the planes defined by the image-taking directions do not have to be parallel to the plane of the ground. The image-taking directions 7 and could therefore be any direction, provided that they effectively make it possible to obtain two images of the osteoarticular system of the patient and provided that they are offset one relative to the other, or in other terms provided that they are not colinear with one another. Thus, the planes of the radiographic images, that is to say the plane of the detectors, can be parallel to one another or offset to one another.

The two detectors 6, 12 are connected to a computerized system 37 or some other electronic control system fitted with:

an input interface comprising at least a keyboard 18 and generally also a mouse (not shown);

an output interface comprising at least a screen 19;

a reconstruction device, e.g. a processor 17, for executing a computer program adapted to implement the method described herein; and a knowledge base of the structure to be reconstructed.

The microcomputer 37 may also be connected to the motor-driven drive means (not shown) contained in the guide 3, and to the sources 5 and 11, so as to control vertical displacement of the frame and the emission of ionizing radiation.

It is to be noted that the two-dimensional radiographic images used in the method according to the invention are "raw" radiographs deriving directly from the detectors. In other terms, these 2D images do not derive from a 2D reconstruction implemented by any volumic imaging technique, such as CT-scanning or MRI.

According to a first embodiment of the invention, the method is a method for designing a spinal implant for a patient having scoliosis.

Figure 3A:
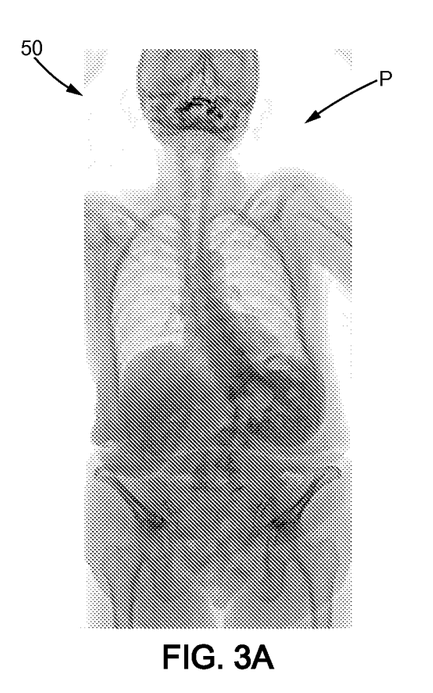
FIGS. 3A and 3B show two radiographs of the spine and of the pelvis of a patient suffering from scoliosis, the radiograph of FIG. 3A being a frontal view and the radiograph of FIG. 3B being a lateral view.
Figure 3B:
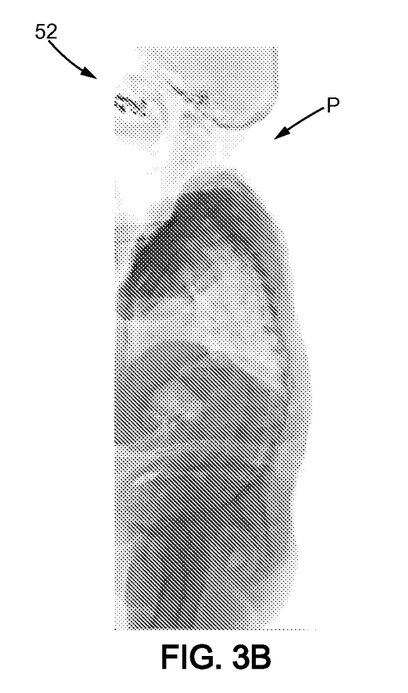

As illustrated on FIGS. 3A and 3B, during step a), two radiographic images 50 (frontal view), 52 (lateral view) of the spine 54 and of the pelvis 56 of patient P are taken by the apparatus 1.

Figure 4A:
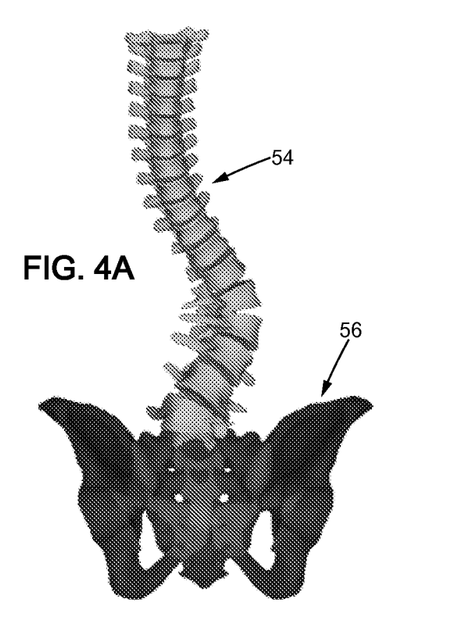
FIGS. 4A and 4B are perspective views of a three-dimensional reconstruction of the spine and pelvis of the patient shown on FIGS. 3A and 3B.
Figure 4B:
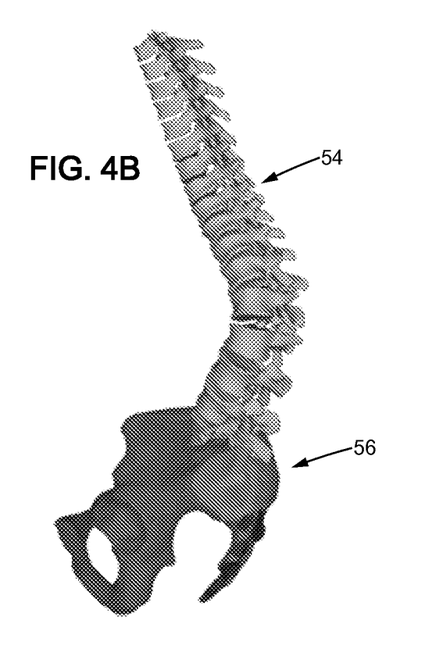

Step b) and part of step c) are then performed automatically by the processor 17 to reconstruct the three-dimensional shape of the spine 54 and pelvis 56 of patient P (FIGS. 4A and 4B).

The reconstruction method used may be one of those described in document EP 1 168 249 B1. Naturally, other types of reconstruction methods may optionally be used in the context of the present invention. Such methods rely on placing in correspondence two representations of a given anatomical part on two calibrated X-ray radiographs.

Next, the practitioner manually identifies the part of the spine 54 on which the spinal implant 58 will be fixed, for example by clicking with the mouse on the chosen vertebrae or by entering their name with the keyboard 18.

Figure 5A:
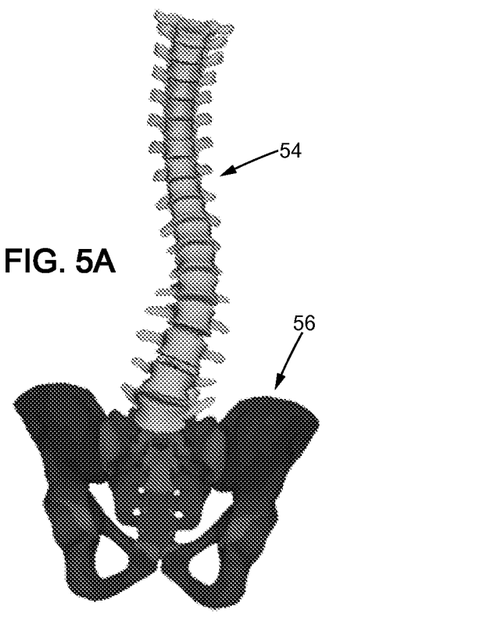
FIGS. 5A and 5B are views similar to those of FIGS. 4A and 4B after correction of the scoliosis of the patient.
Figure 5B:
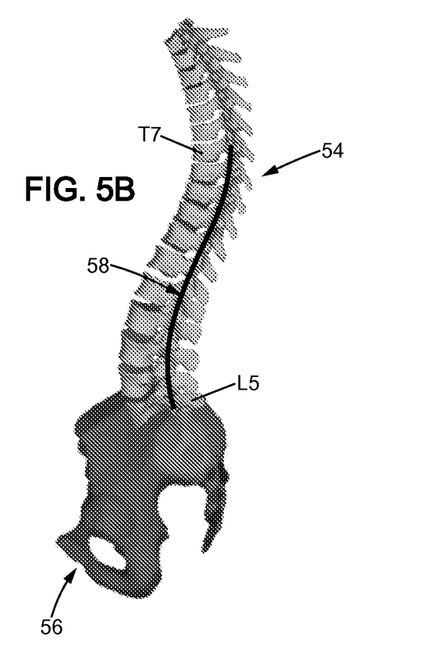

The spinal implant 58 has a rod shape as seen on FIG. 5B.

For example, here, the practitioner decides to position the spinal implant 58 on the lumbar spine between T7 (seventh thoracic vertebra) and L5 (fifth lumbar vertebra).

Therefore, the length between T7 and L5 constitutes a first three-dimensional geometrical feature of patient P.

In this first embodiment, a second three-dimensional geometrical feature of patient P is also determined during step c).

This second geometrical feature is the pelvic incidence of patient P, which is the angle between an axis connecting the centre of the inter-acetabular axis to the centre of the sacral plate and an axis orthogonal to the sacral plate at its centre.

Here, the pelvic incidence is determined in the sagittal plane of patient P.

The length between T7 and L5 and the pelvic incidence are automatically calculated by the processor 17.

At step d), a first and a second three-dimensional size parameter of the spinal implant 58 are determined. More precisely, the first three-dimensional size parameter is the length of the spinal implant 58 and the second three-dimensional size parameter is the curvature of the spinal implant 58.

In order to correct the scoliosis of patient P in an optimal way, the length of the spinal implant 58 is determined to be substantially equal to the length between T7 and L5, and the curvature of the spinal implant 58 is determined to be substantially equal to the lordosis, which is the lumbar curvature of patient P.

The lordosis is related to the pelvic incidence so that on the basis of the pelvic incidence, one can determine the curvature of the spinal implant 58.

For example, according to "Sagittal plane alignment of the spine and gravity: a radiological and clinical evaluation", Legaye J, Duval-Beaupère G, ActaOrthop Belg. 2005 April; 71(2):213-20, the lordosis is given by the following equation:

$$lordosis = (sacral\ slope \times 1.087) + 21.61$$

wherein $$sacral\ slope = (pelvic\ incidence \times 0.5481) + 12.7$$

In a variant, according to "Sagittal plane considerations and the pelvis in the adult patient", Schwab F, Lafage V, Patel A, Farcy J P, Spine (Phila Pa 1976), 2009 Aug. 1; 34(17), the lordosis is given by the following equation:

$$lordosis = pelvic\ incidence + 9$$

Finally, the spinal implant 58 is formed such that it has the length and curvature determined at step d).

In a variant, the spinal implant 58 can be selected among a plurality of existing spinal implants each having different lengths and curvatures, the selected implant being the one having the length and the curvature the closest to the length and curvature determined at step d).

In another variant, the implant can be intended for another part of the spine, for example the thoracic spine, or for another limb, for example the lower limb.

According to a second embodiment of the invention, the method is a method for designing a hip implant for a patient needing hip replacement, for example due to arthritis pain or severe physical joint damage.

During step a), two radiographic images (frontal view and lateral view) of the femur of patient P are taken by the apparatus 1.

Figure 6:
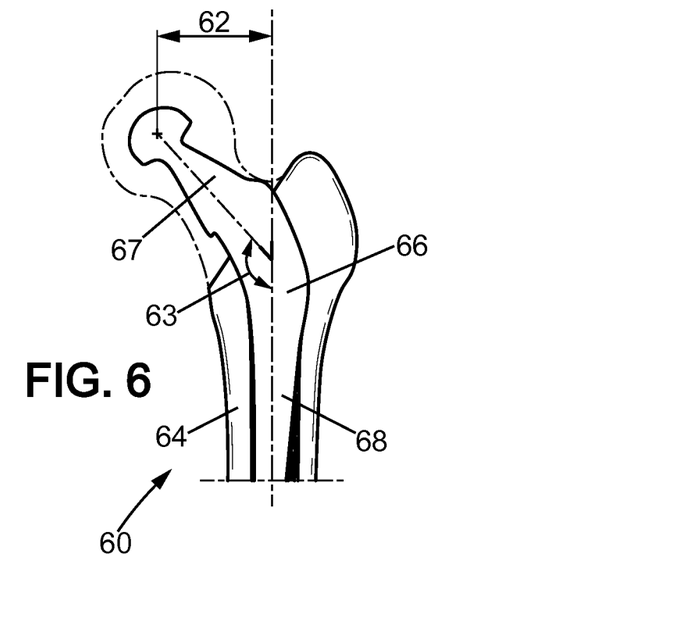
FIG. 6 is a frontal view of a three-dimensional reconstruction of a portion of a femur of a patient needing hip replacement.

Step b) and part of step c) are then performed automatically by the processor 17 to reconstruct the three-dimensional shape of the upper portion of the femur 60 of patient P (FIG. 6).

The reconstruction method used may be the one described in document EP 1 168 249 B1. Naturally, other types of reconstruction methods may optionally be used in the context of the present invention.

At step c), three three-dimensional geometrical features of patient P are automatically determined by the processor 17.

These features are the femoral offset, the femoral neck angle and the internal surface of the femoral shaft 64.

In order to design a reliable and effective hip implant 66, three three-dimensional size parameters are determined during step d).

For example, the hip implant 66 has a substantially "V" shape having two wings 67, 68.

One of the size parameters is the external surface of the second wing 68 which is determined to be substantially equal to the internal surface of the femoral shaft 64.

The second size parameter is the 3D angle between the two wings 67, 68 which is determined to be substantially equal to the femoral neck angle 63.

The last size parameter is the length of the first wing 67 which is determined such that the femoral offset is respected.

Finally, the hip implant 66 is formed such that it has the size parameters determined at step d), for example by molding.

In a variant, three-dimensional geometrical features of the pelvis of the patient can further be determined at step c).

In another variant, the geometrical features are taken on the contralateral hip of the patient, for example when the hip under consideration is too damaged, it is sometimes preferable to reproduce the anatomy of the other hip which is less damaged.

According to a third embodiment of the invention, the method is a method for designing a surgical instrument for the placement and guiding of a bone cutting tool, also called a cutting guide, for a patient needing hip or knee replacement arthroplasty. This third embodiment is described hereunder for the knee.

During step a), two radiographic images (frontal view and lateral view) of the femur of patient P are taken by the apparatus 1.

Figure 7:
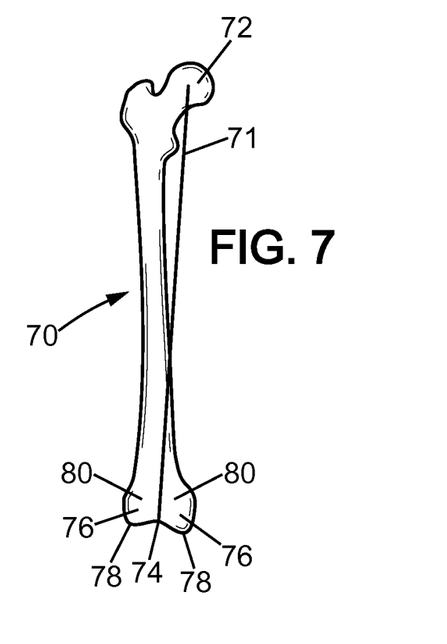
FIG. 7 is a frontal view of a three-dimensional reconstruction of a femur of a patient needing knee replacement arthroplasty.

Step b) and part of step c) are then performed automatically by the processor 17 to reconstruct the three-dimensional shape of the femur 70 of patient P (FIG. 7).

The reconstruction method used may be the one described in document EP 1 168 249 B1. Naturally, other types of reconstruction methods may optionally be used in the context of the present invention.

At step c), five three-dimensional geometrical features of patient P are automatically determined by the processor 17.

One of these features is the position/orientation of the mechanical axis 71 joining the centre of the femoral head 72 and the intercondylar notch 74.

Two other features are the positions of the most distal point 78 of each condyle 76 (FIG. 7).

Two other features are the positions of the most anterior point 80 of each condyle 76.

Figure 8:
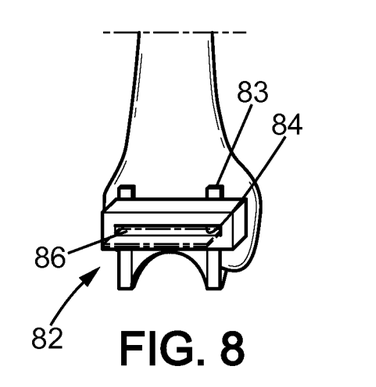
FIG. 8 is a perspective view of a surgical instrument intended to guide a bone cutting tool for the femur of FIG. 7.

In order to design a reliable and effective cutting guide 82, two three-dimensional size parameters are determined during step d).

For example, referring to FIG. 8, the cutting guide comprises a support part 83 intended to rest respectively on the most distal points 78 and on the most anterior points 80 of the condyles 76, and a rectangular slit 84 is provided in the support part 83 to receive the cutting tool which is here a cutting blade 86.

One of the size parameters is the three-dimensional volume of the support part 83 which is determined such that it can rest on the most distal points 78 and on the most anterior points 80 of the condyles 76.

The other size parameter is the three-dimensional volume of the slit 84 which is determined to be substantially orthogonal to the mechanical axis 71 of the femur 70 and about 10 mm above the most distal point 78 of the "ill" condyle.

Finally, the cutting guide 82 is formed such that it has the size parameters determined at step d), for example by molding or by 3D printing.

In a variant, the geometrical features are taken on other points than the most distal points 78 and/or the most anterior points 80 of the condyles.

In another variant, the geometrical features are taken on a number of points different from four.

In another variant, the geometrical feature is a 3D surface and/or volume of the osteoarticular structure.

In another variant, the cutting guide is intended to guide a cutting tool for another part of the femur or for another bone of the patient. Therefore, other geometrical features of the femur or of said another bone (tibia, pelvis, hip, shoulder, etc.) can be determined at step c) depending on the osteoarticular structure under consideration.

In a further embodiment of the invention, the orthopaedic device is a knee implant and a geometrical feature of the femur and/or tibia of the patient is determined at step c).

In a further embodiment of the invention, the orthopaedic device is a shoulder implant and a geometrical feature of the humeral head and/or scapula of the patient is determined at step c).

In a further embodiment of the invention, the orthopaedic device is an ankle implant and a geometrical feature of the foot and/or leg of the patient is determined at step c).

In a further embodiment of the invention, the orthopaedic device is a surgical instrument for the placement of an implant.

In the embodiments described above, the 3D reconstruction of the osteoarticular structure is very accurate but it is possible to provide a simplified 3D reconstruction using only the few anatomical points of interest located at step b).

The present invention thus provides a method which enables to design, reliably and inexpensively, an accurate orthopaedic device which is specific to the patient.

The invention claimed is:

1. A method for designing a patient specific orthopedic device intended for an osteoarticular structure of a patient, based on only two two-dimensional radiographic images of the osteoarticular structure taken respectively in two offset image-taking directions for observing an osteoarticular structure of the patient when in standing position, said radiographic images being raw radiographic images deriving directly from detectors and being not derived from a 2D reconstruction implemented by a volumetric imaging technique such as CT-scanning or MRI, comprising the following steps:
   b) locating anatomical points on the radiographic images by manual identification by practitioner of a relevant part of said osteoarticular structure of patient;
   c) determining at least one three-dimensional geometrical feature of the patient by matching the anatomical points located at step b, by placing in correspondence two representations of a given anatomical part on said two two-dimensional radiographic images which have been calibrated;
   d) determining at least one three-dimensional size parameter of the orthopedic device based on the geometrical feature of the patient determined at step c), said three-dimensional size parameter of the orthopedic device being determined in a three-dimensional space specific to the patient and chosen among a three-dimensional length, a three-dimensional angle, a three-dimensional curvature, a three-dimensional surface and a three-dimensional volume;
   either e1) a step of forming the orthopedic device according to the size parameter determined at step d)
   or e2) a step of selecting the orthopedic device among a plurality of orthopedic devices based on the size parameter determined at step d).

2. A method according to claim 1, further comprising, before step b), a step of a) taking the radiographic images simultaneously.

3. A method according to claim 1, further comprising, before step b), a step of a) taking the radiographic images successively.

4. A method according to claim 1, wherein step c) comprises reconstructing a three-dimensional shape of at least a portion of the osteoarticular structure based on the anatomical points located at step b).

5. A method according to claim 1, wherein the three-dimensional size parameter of the orthopedic device is determined in a plane of a three-dimensional space specific to the patient, said plane being different from each of the planes of the radiographic images.

6. A method according to claim 1, wherein the orthopedic device is chosen among an implant and a surgical instrument for the placement of an implant or of another surgical instrument.

7. A method according to claim 6, wherein the orthopedic device is a spinal implant, a geometrical feature of the pelvis of the patient is determined at step c) and a length and/or a curvature of the spinal implant is determined at step d).

8. A method according to claim 6, wherein the orthopedic device is a hip implant and a geometrical feature of the pelvis and/or femur of the patient is determined at step c).

9. A method according to claim 6, wherein the orthopedic device is a knee implant and a geometrical feature of the femur and/or tibia of the patient (P) is determined at step c).

10. A method according to claim 6, wherein the orthopedic device is a shoulder implant and a geometrical feature of the humeral head and/or scapula of the patient is determined at step c).

11. A method according to claim 6, wherein the orthopedic device is a surgical instrument intended to guide a bone cutting tool, and a geometrical feature of the pelvis, femur and/or tibia of the patient is determined at step c).

12. Computer program product for a data-processing system comprising a set of instructions which, when loaded into the data-processing system, causes the system to perform the steps of the method according to claim 1.

13. A method according to claim 1, wherein the number of said at least one three-dimensional geometrical feature determined at step c) ranges from 1 to 3.

14. An apparatus for designing a patient specific orthopedic device intended for an osteoarticular structure of a patient comprising:
  means for taking two two-dimensional raw radiographic images of the osteoarticular structure in two offset image-taking directions with the patient in a standing position;
  means for locating anatomical points on the two two-dimensional raw radiographic images;
  means for determining at least one three-dimensional geometrical feature of the patient by matching the anatomical points located by the locating means; and
  means for determining at least one three-dimensional size parameter of the orthopedic device based on the geometrical feature of the patient determined by the determining means.

15. An apparatus according to claim 14, further comprising means for taking the radiographic images.

16. An apparatus according to claim 14, wherein the number of said at least one three-dimensional geometrical feature ranges from 1 to 3.

17. A method for designing a patient specific orthopedic device intended for an osteoarticular structure of a patient, the method comprising the following steps:
  a) taking only two two-dimensional raw radiographic images of the osteoarticular structure in two offset image-taking directions with the patient in a standing position, wherein the radiographic images are raw radiographic images deriving directly from detectors and being not derived from a 2D reconstruction implemented by a volumetric imaging technique such as CT-scanning or MRI;
  b) locating anatomical points on the only two two-dimensional raw radiographic images by manual identification by practitioner of a relevant part of said osteoarticular structure of patient;
  c) determining at least one three-dimensional geometrical feature of the patient by matching the anatomical points located at step b, by placing in correspondence two representations of a given anatomical part on said two two-dimensional raw radiographic images which have been calibrated;
  d) determining at least one three-dimensional size parameter of the orthopedic device based on the geometrical feature of the patient determined at step c), said three-dimensional size parameter of the orthopedic device being determined in a three-dimensional space specific to the patient and chosen among a three-dimensional length, a three-dimensional angle, a three-dimensional curvature, a three-dimensional surface and a three-dimensional volume;
  either e1) a step of forming the orthopedic device according to the size parameter determined at step d)
  or e2) a step of selecting the orthopedic device among a plurality of orthopedic devices based on the size parameter determined at step d).

* * * * *